United States Patent [19]

Cai et al.

[11] Patent Number: 5,399,771
[45] Date of Patent: Mar. 21, 1995

[54] PROCESS OF SYNTHESIZING BINAPHTHYL DERIVATIVES

[75] Inventors: Dongwei Cai, Edison; Joseph F. Payack, Somerset; Thomas R. Verhoeven, Cranford, all of N.J.

[73] Assignee: Merck & Co., Inc., Rahway, N.J.

[21] Appl. No.: 252,306

[22] Filed: Jun. 1, 1994

[51] Int. Cl.$^6$ .............................................. C07F 9/02
[52] U.S. Cl. ............................................... 568/17
[58] Field of Search ......................................... 568/17

[56] References Cited

U.S. PATENT DOCUMENTS

| | | | |
|---|---|---|---|
| 4,691,037 | 9/1987 | Yoshikawa et al. | 568/17 |
| 4,879,416 | 11/1989 | Puckette et al. | 568/17 |
| 4,956,055 | 9/1990 | Puckette et al. | 568/17 |
| 5,026,886 | 6/1991 | Stavinoha et al. | 568/17 |
| 5,231,202 | 7/1993 | Hayashi et al. | 568/17 |
| 5,268,492 | 12/1993 | Yamamoto et al. | 568/17 |
| 5,312,939 | 5/1994 | Hori et al. | 568/17 |

OTHER PUBLICATIONS

J A C S 93(22): 5908–5910 (1971) M. F. Semmelhack, et al. "Synthesis with Zerovalent Nickel. Coupling of Aryl Halides with Bis(1,5-cyclooctadiene)nickel (0)".
Tet. Let. 34(10): 1615–1616 (1993) Ohta, T. et al. "A Convenient Synthesis of Optically Pure Dimethyl 1,1′-Binaphthalene-2,2′-dicarboxylate from 1,1′-Binaphthalene-2,2′-diol".
J A C S 98(23): 7255–7265 (1976) Komiya, S. et al. "Reductive Elimination and Isomerization of Organogold Complexes . . . ".
J. Org. Chem. 58: 1945–1948(1993) Uozumi, Y. et al. "Synthesis of Optically Active 2-(Diarylphosphino)-1,-1′-binaphthyls, Efficient Chiral Monodentate Phosphine Ligands".
Bull. Chem. Soc. Jpn. 66(7):2002–2005 (1993) Kawashima, M. et al. "Epimerization–Crystallization Method in Optical Resolution of 2,2′-Dihydroxy-1,1′-binaphthyl, and Kinetic Study".
Tet. Let. 31 (44): 6321–6324 (1990). Kurz, L. et al. "Stereospecific Functionalization of (R)-(−)-1,1′-Bi-2-Naphthol Triflate".
J. A. C. S. 102(15): 4933–4941 (1980). Gille, A. et al. "Mechanisms of 1,1-Reductive Elimination from Palladium".

*Primary Examiner*—James H. Reamer
*Attorney, Agent, or Firm*—Richard C. Billups; Mark R. Daniel; Joseph F. DiPrima

[57] ABSTRACT

A process of synthesizing a compound of the formula 1:

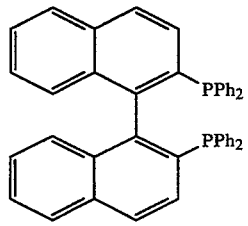

is disclosed, which comprises reacting a compound of the formula 2:

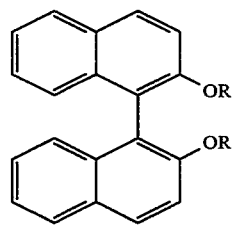

with diphenylphosphine in the presence of an amine base and a nickel catalyst to produce a compound of formula 1.

15 Claims, No Drawings

PROCESS OF SYNTHESIZING BINAPHTHYL DERIVATIVES

BACKGROUND OF THE INVENTION 2,2'-Bis(diphenylphosphino)-1,1'-binaphthyl (BINAP) has become an important chiral ligand for catalytic asymmetric induction. Its wide application has been somewhat limited due to the scarce supply. The present invention relates to a simple and inexpensive process for the synthesis of BINAP which avoids the necessity of a multistep synthesis and minimizes the formation of secondary products.

SUMMARY OF THE INVENTION

A process of synthesizing a compound of formula 1 is disclosed.

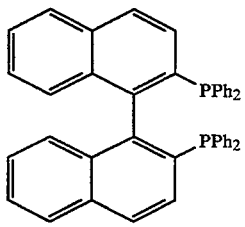

A compound of the formula 2:

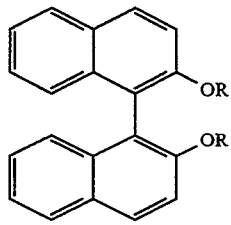

wherein R is selected from the group consisting of triflate, mesylate and tosylate, is reacted with diphenylphosphine in the presence of an amine base and a nickel catalyst to produce a compound of formula 1.

DETAILED DESCRIPTION OF THE INVENTION

As used herein, the following terms and definitions apply.

The abbreviation "Ph" refers to phenyl.

BINAP stands for the chemical 2,2'-Bis(diphenylphosphino)-1,1'-binaphthyl which has the structural formula 1:

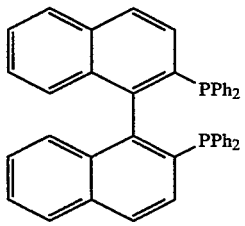

Triflate refers to the leaving group trifluoromethanesulfonate. Mesylate refers to the leaving group methanesulfonate. Tosylate refers to the leaving group toluenesulfonate.

The catalyst which is included herein is a nickel catalyst. Such catalysts are selected from the group consisting of: $NiCl_2$.bis(diphenyl)phosphinyl $C_{1-4}$ alkanes, $NiBr_2$, $NiCl_2$, $NiCl_2$-bis(diphenyl)phosphinyl ferrocene, abbreviated $NiCl_2$/dppf; $NiCl_2$-bis(triphenylphosphine), abbreviated $NiCl_2/(Ph_3P)_2$; Ni-tetrakis (triphenylphosphine), abbreviated $Ni(Ph_3P)_4$; Ni-tetrakis (triphenylphosphite), abbreviated $Ni[(PhO)_3]_4$ and Ni-dicarbonyl bis(triphenyl)phosphine, abbreviated $Ni(CO)_2(Ph_3P)_2$.

The preferred catalysts for use herein are the $NiCl_2$-bis(diphenyl)phosphinyl $C_{1-4}$ alkanes. In particular, the $C_{2-3}$ alkanes are preferred. Hence, the preferred catalysts are $NiCl_2$.bis(diphenyl)phosphinylethane, which is abbreviated "$NiCl_2$dppe", and $NiCl_2$.bis(diphenyl)phosphinylpropane, which is abbreviated "$NiCl_2$dppp". The most preferred catalyst for use in the process described herein is $NiCl_2$dppe.

In one embodiment of the invention, an R(+) isomer of the compound of formula 1 is synthesized. An R(+) isomer of a compound of formula 2:

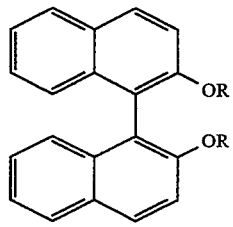

wherein R is as previously defined, is reacted with diphenylphosphine in the presence of an amine base and a nickel catalyst to produce the R(+) isomer of a compound of formula 1.

In another embodiment of the invention, the S(−) isomer of a compound of the formula 2:

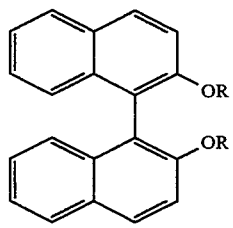

wherein R is as previously defined, is reacted with diphenylphosphine in the presence of an amine base and a nickel catalyst to produce the S(−) isomer of a compound of formula 1.

The preferred process which is described herein directly converts the R(+) chiral ditriflate of 1,1'-bi-2-naphthol to R(+) chiral BINAP 1. Likewise, another preferred process directly coverts the S(−) chiral ditriflate of 1,1'-bi-2-naphthol to the (S) - chiral BINAP 1. Essentially no racemization occurs in these preferred embodiments.

Diphenylphosphine is added in a suitable solvent at a temperature which is effective for allowing the formation of BINAP 1 in the presence of an amine containing base and the nickel catalyst. Since diphenylphosphine is a good ligand for nickel, the amount of diphenylphosphine present in the reaction medium can significantly effect the reaction rate, slowing the reaction if the amount of diphenylphosphine is too great. When the diphenylphosphine is added stepwise during the reaction, the reaction can be completed in about 2 days. The coupling reaction slows down at later stages, possibly due to product and impurity poisoning. The reaction is typically completed in 3~4 days if all the diphenylphosphine is added at once.

Suitable solvents include those which do not substantially oxidize the diphenylphosphine at the appropriate temperature, while maintaining the desired solubility. Polar solvents are preferred. Illustrative of these solvents are dimethylformamide, acetonitrile and N-methylpyrrolidinone. The most preferred solvent is dimethylformamide (DMF).

The amine base and amount of the base included in the reaction influence the reaction selectivity and reaction rate. Amine bases as used herein include the following: diazabicyclo(2.2.2)octane (DABCO), triethylamine, diisopropylethylamine, tri n-propylamine, and tri n-butylamine. The preferred amine bases are DABCO and triethylamine. The most preferred base is DABCO.

The reaction is typically run at a temperature which allows the reaction to proceed without producing undesirable quantities of side products. The temperature range is from about 80° to about 120° C., with about 100° C. being preferred.

BINAP has been useful in the preparation of antibiotics, in particular, carbapenems. In many carbapenem antibiotics, a side chain is present at position 2, which contains a hydroxyalkylpyrrolidine group. Such hydroxyl groups can be produced by reacting a carbonyl at the appropriate position with a compound of formula 1. This reaction is typically conducted in an alcoholic solvent, and in the presence of an acid.

The invention is further described in connection with the following Examples.

PREPARATIVE EXAMPLE 1

Resolution of Trans-1,2-diaminocyclohexane (chxn)

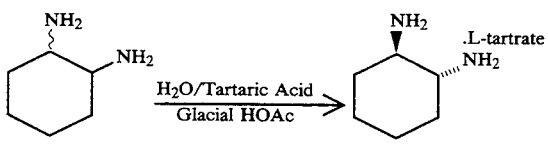

Racemic chxn (120 mL, 1.0 mol) was combined with water (200 mL) and L-tartaric acid (75 g, 0.5 mol). The mixture exothermed to 45° C., then was heated to 90° C. until a homogeneous solution resulted (~30 min.). The solution was cooled to 80° C., and then glacial acetic acid (50 mL, 0.873 mol) was added over 10 min., keeping the temperature below 96° C. White crystals formed during the acetic acid addition.

The mixture was cooled to 0° C. and was aged at that temperature for 2 h. The crystals were collected and were washed with 0° C. water (40 mL) and 0° C. ethanol (100%, 2×50 mL). The filter cake was partially dried via suction, then was recrystallized from 1.20 L of water heated to 97° C., and then aged at ambient temperature for 18 h. The crystals were collected at ambient temperature, washed with water (40 mL) and 0° C. ethanol (40 mL).

Drying the crystals at 60° C. in a vacuum oven yielded 75.7 g of 1:1 (R,R)-chxn: L-tartrate complex.

PREPARATIVE EXAMPLE 2

The complex generated in Preparative Example 1 (55.7 mmol, 14.7 g) was slurried in methanolic KOH (77 g of a 8.1 wt % solution: 111 mmol) and was stirred for 18 h. The potassium tartrate was removed via filtration, and the chxn solution was evaporated, producing 5.6 g of (R,R)-chxn as a colorless oil which crystallized upon standing.

PREPARATIVE EXAMPLE 3

Resolution of 1,1'-Bi-2-naphthol

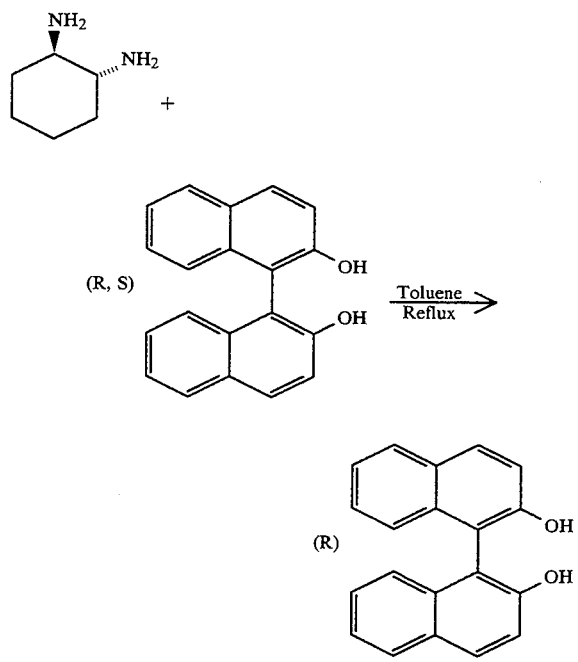

A mixture of (R,R)-chxn (372 mg, 3.26 mmol), racemic binaphthol (934 mg, 3.25 mmol), and toluene (13 mL) was heated to reflux. After 45 min. all of the material was in solution. The solution was cooled to room temperature, then aged 1.5 h. White crystals formed, which were collected. The mother liquors contained chxn/S-binaphthol in 95% (assay) recovery, 98.4% ee. The collected crystals consisted of 90% ee R-binaphthol/chxn/toluene (1/1/1)complex in 105% recovery (849 mg).

The R-binaphthol complex was racemized by refluxing in 6.8 mL toluene for 48 h. Cooling to rt and filtering as above gave mother liquors of 99% ee.

PREPARATIVE EXAMPLE 4

Preparation of Ditriflate of 1,1'-Bi-2-naphthol

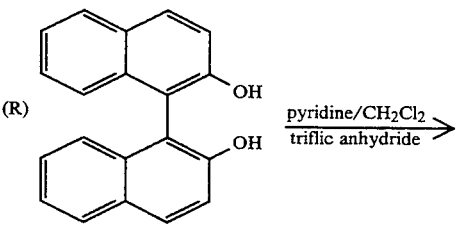

-continued

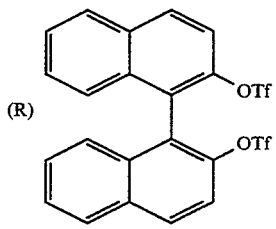

To a solution of (R)-(+)-1,1'-bi-2-naphthol from Preparative Example 3 (42.3 g, 0.15 mol) and pyridine (36 mL, 0.45 mol) in dry methylene chloride (300 mL) was added triflic anhydride (100 g, 0.35 mol) dropwise at around 5°~10° C. After the addition, the reaction solution was stirred at room temperature for 8 hrs, and hexane (300 mL) was added. The resulting mixture was filtered through a pad of silica gel (500 mL silica gel in 600 mL funnel). The silica gel was washed with additional solvent (1 L, 1:1 mixture of hexane and CH$_2$Cl$_2$). The resulting filtrate was concentrated to to produce 1,1'-bi-2-naphthol ditriflate as a white solid (82.7 g).

EXAMPLE 1

Preparation of (R)-(+)-BINAP

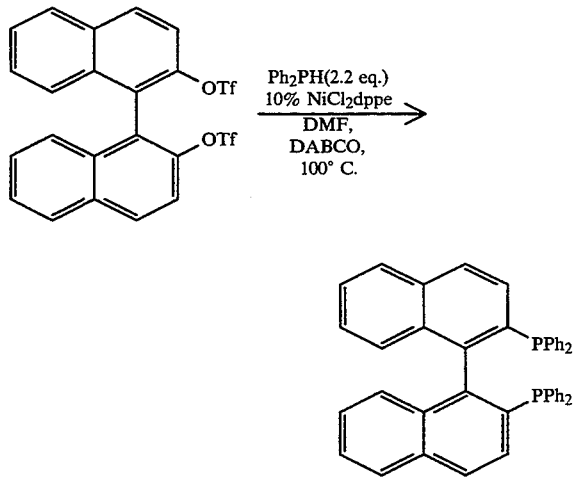

To a solution of NiCl$_2$dppe (530 mg, 1 mmol) in DMF (20 mL) was added diphenylphosphine (1 ml, 5.75 mmol) at room temperature, then the resulting solution was heated at 100° C. After heating at 100° C. for 30 mins, a solution of the chiral ditriflate from Preparative Example 4 (5.50 g, 10 mmol) and DABCO (4.5 g, 40 mmol) in DMF (30 mL) was added at once and resulting dark green solution was kept at 100° C. and three additional portions of diphenylphosphine (3×1 mL) were added at 1 hr, 3 hrs, and 7 hrs later. The reaction was kept at 100° C. until the starting material ditriflate was completely consumed (2~3 days), then the dark brown solution was cooled down to room temperature and stirred at room temperature for 2 hrs, and finally cooled down to 0°~5° C. with an ice bath.

The desired product 1 was filtered and the filter cake was washed with methanol (2×10 mL) and dried under vacuum. The isolated product (4.95 g) was a white or off white crystalline compound with chemical purity around 95~97 area % (HPLC, 220 nm).

EXAMPLE 2

Substitute NiCl$_2$dppp for NiCl$_2$dppe in the process of Example 1 to produce the desired product 1.

What is claimed is:

1. A process of synthesizing a compound of formula 1:

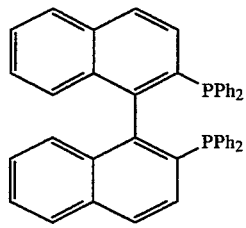

comprising reacting a compound of the formula 2:

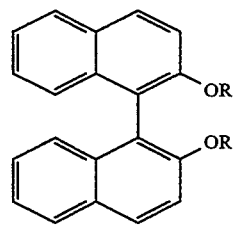

wherein R is selected from the group consisting of triflate, mesylate and tosylate,
with diphenylphosphine in the presence of an amine base and a nickel catalyst to produce a compound of formula 1.

2. A process in accordance with claim 1 wherein the nickel catalyst is selected from the group consisting of: NiCl$_2$.bis(diphenyl)phosphinyl C$_{1-4}$ alkane, NiBr$_2$, NiCl$_2$, NiCl$_2$-bis(diphenyl)phosphinyl ferrocene, NiCl$_2$-bis(triphenylphosphine), Ni-tetrakis triphenylphosphine, Ni-tetrakis triphenylphosphite and Ni-dicarbonyl bis(triphenyl)phosphine.

3. A process in accordance with claim 2 wherein the catalyst is a NiCl$_2$.bis(diphenyl)phosphinyl C$_{1-4}$ alkane.

4. A process in accordance with claim 3 wherein the NiCl$_2$.bis(diphenyl)phosphinyl C$_{1-4}$ alkane is NiCl$_2$.bis(-diphenyl)phosphinyl ethane or NiCl$_2$.bis(diphenyl)-phosphinyl propane.

5. A process in accordance with claim 4 wherein R represents triflate.

6. A process in accordance with claim 1 wherein the amine base is selected from the group consisting of: 1,4-diazabicyclo[2.2.2]octane, triethylamine, diisopropyl ethyl amine, tri-n-propylamine and tri-n-butylamine.

7. A process in accordance with claim 1 wherein the reaction is conducted in a solvent selected from the group consisting of: dimethylformamide, acetonitrile and N-methylpyrrolidinone.

8. A process in accordance with claim 7 wherein the amine base is 1,4-diazabicyclo[2.2.2]octane or triethylamine.

9. A process in accordance with claim 8 wherein the solvent is dimethylformamide.

10. A process in accordance with claim 2 wherein the solvent is dimethylformamide.

11. A process in accordance with claim 5 wherein the amine base is 1,4-diazabicyclo[2.2.2]octane or triethylamine.

12. A process of synthesizing a compound of formula 1:

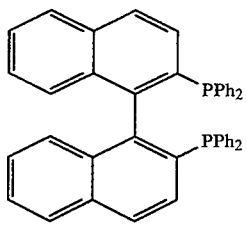

comprising reacting the R(+) isomer of a compound of the formula 2:

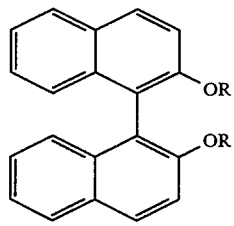

wherein R is selected from the group consisting of triflate, mesylate and tosylate, with diphenylphosphine in the presence of an amine base and a nickel catalyst to produce the R(+) isomer of a compound of formula 1.

13. A process in accordance with claim 12 wherein the reaction is conducted without substantial racemization.

14. A process of synthesizing a compound of formula 1:

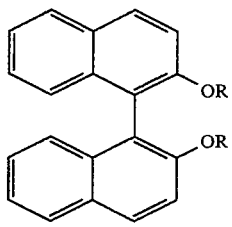

comprising reacting the S(−) isomer of a compound of the formula 2:

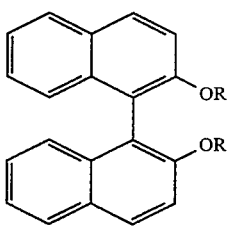

wherein R is selected from the group consisting of triflate, mesylate and tosylate, with diphenylphosphine in the presence of an amine base and a nickel catalyst to produce the S(−) isomer of a compound of formula 1.

15. A process in accordance with claim 14 wherein the reaction is conducted without substantial racemization.

* * * * *

UNITED STATES PATENT AND TRADEMARK OFFICE
CERTIFICATE OF CORRECTION

PATENT NO. : 5,399,771
DATED : Mar. 21, 1995
INVENTOR(S) : Dongwei Cai, et al

It is certified that error appears in the above-indentified patent and that said Letters Patent is hereby corrected as shown below:

In Claim 14, at column 8, lines 3-16 delete the structure:

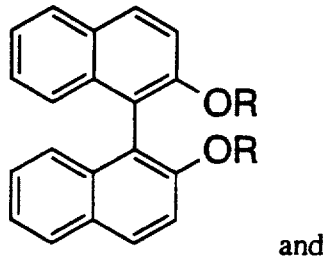

and replace the structure with the following:

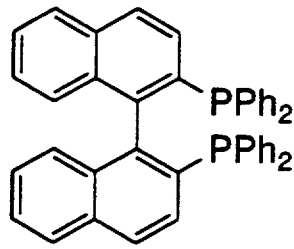

Signed and Sealed this

Nineteenth Day of September, 1995

Attest:

BRUCE LEHMAN

Attesting Officer    Commissioner of Patents and Trademarks